United States Patent [19]

Siren

[11] Patent Number: 5,057,507

[45] Date of Patent: Oct. 15, 1991

[54] METHOD OF ALLEVIATING BONE DAMAGE WITH INOSITOLTRIPHOSPHATE

[75] Inventor: Matti Siren, Montagnola/Lugano, Switzerland

[73] Assignee: Perstorp AB, Perstorp, Sweden

[21] Appl. No.: 645,233

[22] Filed: Jan. 24, 1991

Related U.S. Application Data

[60] Division of Ser. No. 492,740, Mar. 13, 1990, Pat. No. 5,015,634, Continuation-in-part of Ser. No. 173,985, Mar. 28, 1988, Pat. No. 5,019,566, and a continuation-in-part of Ser. No. 251,566, Sep. 30, 1988, Pat. No. 5,123,348, and a continuation-in-part of Ser. No. 367,968, Jun. 19, 1989.

[51] Int. Cl.$^5$ ............................................. A01N 57/00
[52] U.S. Cl. .................................................... 514/103
[58] Field of Search ........................................ 514/103

[56] References Cited

U.S. PATENT DOCUMENTS

| 273,938 | 11/1955 | Buchwalter | 167/55 |
|---|---|---|---|
| 3,591,665 | 7/1971 | Kimura et al. | 260/983 |
| 4,473,563 | 9/1984 | Nicolau et al. | 424/224 |
| 4,734,283 | 3/1988 | Siren | 424/439 |
| 4,735,902 | 4/1988 | Siren | 435/188 |
| 4,735,936 | 4/1988 | Siren | 514/103 |
| 4,777,134 | 10/1988 | Siren | 435/155 |
| 4,797,390 | 1/1989 | Siren | 514/103 |
| 4,851,560 | 7/1989 | Siren | 558/155 |
| 5,003,098 | 3/1991 | Siren et al. | 558/155 |

OTHER PUBLICATIONS

Suematsu et al., Biochem. and Biophys. Res. Comm., 120, No. 2, 481–485 (1984).
Desjobert, Bull. Ste. Chim. Biol., 36, 1293–1299 (1954).
Streb et al., Nature, 306, 67–68 (1983).
Irvine et al., Biochem. J., 223, 237–243 (1984).
Lim et al., Biochim. and Biophys. Acta, 302, 316–328.
Tomlinson et al., Biochemistry, 1, No. 1, 166–171 (1973).
Kerr et al., Arch. of Biochem. and Biophys. 96, 347–352 (1962).

Primary Examiner—Stanley J. Friedman
Assistant Examiner—T. J. Criares
Attorney, Agent, or Firm—Scully, Scott, Murphy & Presser

[57] ABSTRACT

A method of preventing or alleviating tissue or bone damage in mammals is disclosed. The method comprises administering, to a mammal, a tissue damage or a bone damage preventing or alleviating effective amount of a pharmaceutical composition which includes at least one isomer of inositol trisphosphate.

8 Claims, No Drawings

METHOD OF ALLEVIATING BONE DAMAGE WITH INOSITOLTRIPHOSPHATE

REFERENCE TO RELATED APPLICATIONS

This is adivisional of copending application Ser. No. 492,470 filed on Nov. 13, 1990 now U.S. Pat. No. 5,015,634, which is a continuation-in-part of U.S. patent application Ser. No. 173,985 filed March 28, 1988, now U.S. Pat. No. 5,019,566; U.S. patent application, Ser. No. 251,566 filed Sept. 30, 1988, now U.S. Pat. No. 5,012,348; and U.S. patent application Ser. No. 367,968 filed June 19, 1989, pending.

FIELD OF THE INVENTION

The present invention relates to a method or alleviating different conditions in the body by administering thereto a pharmaceutical composition comprising an amount of at least one specific isomer of inositoltrisphosphate sufficient to obtain said prevention or alleviation.

BACKGROUND OF THE INVENTION

Injury or destruction of tissues should be understood as damage to an aggregation of specialized cells with a particular function both internally and externally in the body, such as different organs or parts of these, vessels, skin etc.

Tissue damage involves a complex series of events such as dilation of vessel walls e.g. arterioles, capillaries and venules, increased permeability of fluids including e.g. plasma proteins and increased blood flow. Increased vascular leakage often results in extravasation an oedema formation which characterize the damage of different tissues.

Often tissue damage is characterized by signs of pain, heat, redness, swelling and loss of function.

Tissue damage is not defined as a disease per se but is often a component in different diseases of both acute and chronic nature.

Damage of tissues can be induced in many ways. Inducing factors can be correlated with mechanical effects, immunological effects or chemical effects. Microorganisms such as virus, bacteria and fungus can induce tissue damage and exposure to heat, fire, radiation, cold and blows most often results in such damage. Many diseases like asthma, eczema, psoriasis, rheumatoid arthritis, diabetes and arteriosclerosis also involve different types of tissue damage.

The existing treatment of diseases connected to tissue damage are based on drugs such as non steroid antiinflammatory drugs (NSAID), steroids, antibiotics and cytostatics. In some cases also surgical therapy is used.

Existing drugs often suffer from limited effectiveness in combination with serious side effects. Toxic effects appearing from the treatment with NSAID:s can consist of gastrointestinal side effects, allergic reactions and side effects in the central nervous system. Treatment with steroids often results in side effects such as osteoporosis and fractures, increased susceptibility to infections and peptic ulcerations.

From the U.S. Pat. No 4,735,936 a pharmaceutical composition comprising as a pharmaceutically active ingredient at least one isomer of inositoltrisphosphate is known. In said patent the effect of this pharmaceutical composition is shown for different areas, such as cardiovascular diseases and arthritis.

SUMMARY OF THE INVENTION

According to the present invention it has surprisingly become possible to overcome and reduce the above mentioned injuries and destructions of tissues as a method of preventing or alleviating tissue damage has been brought about. At said method a pharmaceutical composition comprising an amount of at least one specific isomer of inositoltrisphosphate ($IP_3$) sufficient to obtain said prevention or alleviation is administered to a human or an animal.

Preferred embodiments of the invention relate to a method of preventing or alleviating tissue damage related to oedema formation, vascular leakage, burns, rhinitis and asthma by administering to a human or an animal a pharmaceutical composition comprising an amount of at least one specific isomer of $IP_3$ sufficient to obtain said prevention or alleviation.

In addition the present invention also covers a method of preventing or alleviating bone disorders by administering a pharmaceutical composition comprising an amount of at least one specific isomer of $IP_3$ sufficient to obtain said prevention or alleviation.

Preferred embodiments of the invention relate to a method of preventing or alleviating bone disorders related to bone mineralization, osteoporosis, bone erosion and periostitis by administering said pharmaceutical composition.

DETAILED DESCRIPTION OF PREFERRED EMBODIMENTS

As examples of conditions, which the method according to the invention is useful to prevent or alleviate, there are mentioned the following conditions:

Tissue damage induced mechanically by heat and fire such as burns of first, second or third degree, trauma i.e. wounds or injuries caused by physical damage, or cold; Tissue damage induced chemically or by microorganisms such as radiation, sepsis and injuries caused by e.g. bee-stings, snake-bites etc; Tissue damage in diseases where the immunological component is strongly expressed such as rhinitis, hayfever, asthma, psoriasis, vasculitis and eczema. Furthermore the invention relates to a method of preventing or alleviating tissue damage related to erythema and herpes, injuries caused by or following surgery and operations of grafts, catheters etc. and injuries caused by or occurring in the border zone of an infarct of cardiac type, cerebral type or any other type. Other injuries of tissues related to diseases such as uveitis, otitis, stomatitis, peritonitis, sinusitis, gastro-enteritis, colitis and cystitis are also related to the invention.

The method of preventing or alleviating tissue damage is effective against tissue damage connected to the above mentioned conditions but also to other conditions where tissue damage occurs.

The present invention also relates to a method of preventing or alleviating bone disorders by administering to a human or an animal an amount of a specific isomer of $IP_3$ sufficient to obtain said prevention or alleviation. As examples of conditions related to bone disorders the following are mentioned:

Osteroporosis; degenerative joint diseases and osteitis, e.g. Paget's disease; osteomalacia and rickets; conditions characterized by abnormal levels of calcium, phosphorus, alkaline phosphatase and conditions attributable to changed function and metabolism of different glands such as the parathyroid, the thyroid and the pituitary;

erosion of bones e.g. destruction of articular surfaces; different forms of periostitis and arthrosis.

The production of IP$_3$ and the isolation of the different isomers thereof are disclosed in the U.S. Pat. No. 4,777,134. The IP$_3$ isomers can also be produced by synthetic methods, chemically or enzymatically, starting with e.g. inositol and a phosphorus source. Furthermore, microbiological production methods including hybrid DNA-techniques of IP$_3$ are also suitable.

The structure of IP$_3$ and the different isomers thereof are disclosed in the U.S. Pat. No. 4,735,936 and the U.S. Pat. No. 4,797,390.

It is suitable that the composition used according to the invention exists in unit dosage form. Tablets, granules or capsules are suitable administration forms for such unit dosage. Furthermore, tablets and granules can easily be surface treated such as to provide an enteric coating to prevent an uncontrolled hydrolysis in the stomach and to bring about a desired absorption in the intestine. Other suitable administration forms are slow release or transdermal administration, nasal, rectal, intra-articular, topical, intraperitoneal, and subcutaneous administrations. A usual pharmaceutically acceptable additive, excipient and/or carrier can be included in the medicament. The tablets or granules can also contain a disintegrant which causes the tablets or the granules, respectively, to disintegrate easily in the intestine. In certain cases, especially in acute situations, it is preferable to use the unit dosage in the form of a solution for intravenous administration.

The pharmaceutical composition used in the method can also consist as such of IP$_3$ solely without any additive, excipient or carrier.

If desired, the composition can be free of other inositol phosphates, IP$_1$, IP$_2$, IP$_4$, IP$_5$ and IP$_6$. Accordingly, the mixture of IP$_3$ isomers can have a purity of 90-100%, such as 93-100% or preferably 95-100%.

Alternatively, the pharmaceutical composition used in the method can consist of or comprise one or more specific IP$_3$ isomers, each present in substantially pure form. Thus, the different isomers can be isolated from each other in substantially pure form, which means that they have a purity of 80-100%, such as 82-100% or 85-100%, preferably 90-100%. Since the isomers can be produced in pure form they can be mixed in any proportion, of course.

The composition can consist of IP$_3$, wherein said IP$_3$ is provided by at least one of IP$_6$, IP$_5$ or IP$_4$ and a degradative substance such as an enzyme suitable to form IP$_3$.

It is in most cases suitable that the IP$_3$-isomer or isomers in the composition used in the method according to the invention is present in salt form in order not to affect the mineral balance negatively. The salt should preferably consist of a sodium, potassium, calcium, zinc or magnesium salt or a mixture of two or more of these salts.

For the above mentioned reasons it is also an advantage if the medicament contains a surplus or an extra addition of at least one pharmaceutically acceptable salt of calcium, zinc or magnesium with a mineral acid or organic acid. This is especially valuable for elderly persons who are often deficient in these minerals.

For administration to human patients appropriate dosages can routinely be determined by those skilled in this art by extension of the results obtained in animals at various dosages. The preferred dosage for humans falls within the range of 0.1 to 1000 mg, especially 0.1-200 mg IP$_3$/day/kg body weight.

The pharmaceutical composition used in the method according to the invention usually contains 0.01-1.5 g, such as 0.05-1.3 or preferably 0.1-1 g of IP$_3$ per unit dosage.

The composition used according to the present invention contains at least one, sometimes two or more of the following substances, which correspond to the essential IP$_3$-isomer or isomers mentioned above:

D-myo-inositol-1,2,6-trisphosphate of the formula

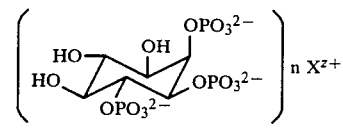

where X is hydrogen, at least one univalent, divalent or multivalent cation, or a mixture thereof, n is the number of ions, and z is the charge of the respectively ion;

Myo-inositol-1,2,3-trisphosphate of the formula

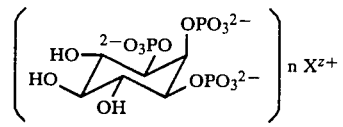

where X, n and z have the above mentioned meaning;

L-myo-inositol-1,3,4-trisphosphate of the formula

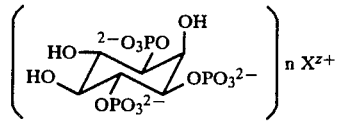

where X, n and z have the above mentioned meaning.

In each of the above formulas n ranges between 6 to 1 inclusive and z ranges from 1 to 6 inclusive. Preferably, n is between 3 to 6 inclusive and z is 3, 2 or 1. Of above isomers D-myo-inositol-1,2,6-trisphosphate is preferred.

Other inositol trisphosphate isomers that may be utilized in the present invention as the active IP$_3$ ingredient in the composition have the structural formula

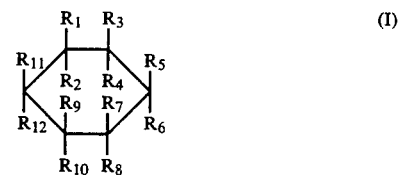

(I)

One group of inositol trisphosphate compounds is defined by the structural formula (I) where three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen.

Another group of inositol trisphosphates is defined by the structural formula (I) where three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen.

Still another group of inositol trisphosphates is defined by the structural formula (I) where three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen.

Yet another group of inositol trisphosphates is defined by the structural formula (I) where three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen.

Still yet another group of inositol trisphosphates is defined by the structural formula (I) where three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol trisphosphates is defined by the structural formula (I) where three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet another group of inositol trisphosphates is defined by the structural formula (I) where three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen.

Finally, another group of inositol trisphosphates is defined by the structural formula (I) where three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol trisphosphate compounds within the contemplation of the above formula include compounds having the structural formula (I) where $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen;

$R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen;

$R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen;

$R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_{12}$ are phosphate, $R_3$, $R_8$ and $R_{10}$ are hydroxyl and $R_2$, $R_4$, $R_6$, $R_7$, $R_9$ and $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen;

$R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$ and $R_{12}$ are hydroxyl and $R_2$, $R_4$, $R_6$, $R_7$, $R_{10}$ and $R_{11}$ are hydrogen;

$R_3$, $R_5$ and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$ and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$ and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_3$, $R_5$ and $R_9$ are phosphate, $R_1$, $R_8$ and $R_{12}$ are hydroxyl and $R_2$, $R_4$, $R_6$, $R_7$, $R_{10}$ and $R_{11}$ are hydrogen;

$R_5$, $R_9$ and $R_{12}$ are phosphate, $R_1$, $R_3$ and $R_8$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$ and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$ and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$ and $R_8$ are hydroxyl and $R_2$, $R_4$, $R_6$, $R_7$, $R_{10}$ and $R_{11}$ are hydrogen;

$R_5$, $R_8$ and $R_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_9$ and $R_{12}$ are phosphate, $R_1$, $R_5$ and $R_8$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$ and $R_9$ are hydroxyl and $R_2$, $R_4$, $R_6$, $R_7$, $R_{10}$ and $R_{11}$ are hydrogen; and $R_8$, $R_9$ and $R_{12}$ are phosphate, $R_1$, $R_3$ and $R_5$ are hydroxyl and $R_2$, $R_4$, $R_6$, $R_7$, $R_{10}$ and $R_{11}$ are hydrogen.

The above formula describes specific isomers of inositol trisphosphate where the inositol is selected from the group myoinositol, cisinositol, epiinositol, alloinositol, neoinositol, mucoinositol, chiroinositol and scylloinositol.

IP$_3$ may be the sole pharmaceutically active ingredient in the composition used. However, also other pharmaceutically active ingredients can be present therein. The amount of IP$_3$ should then constitute 5 to 95 or 15 to 80, such as 25 to 60 percent by weight of said active ingredients.

One function of the use of the method is to reverse, prevent or alleviate damage to membranes of different cell types, but especially cell membranes of platelets and endothelial cells, macrophages and leucocytes such as white blood cells, lymphocytes and neutrophils. The use of the method results in an improved stabilization, a decreased susceptibility to deformation and an improved function of the cell types. Furthermore, parameters such as aggregability and adhesion to e.g. vessel walls are decreased.

Cellular mediators such as histamine, bradykinin, platelet activating factors and cytokines are also normalized when the composition is used. Other results of the use of the use of the method are regulation of membrane fluidity, the incorporation of components such as cholesterol and the production, incorporation and balance between different phospholipids.

Another result of the use of the medicament is the regulation of the electrolyte balance of the cell. As examples, regulation of intracellular levels of calcium, potassium, chloride, phosphate etc. can be mentioned.

Furthermore the use of the method according to the invention results in preventing and alleviating specific types of cell to cell attachment, which are deleterious to the body. For example leucocytes, a group of cells with diverse functions, are activated under some physiological and pathological conditions and adhere to other cell types such as endothelial cells. The adhesion process leads to different forms of cytotoxicity, phagocytosis, chemotaxis and induction of cell proliferation and differentiation. These events often leads to conditions described above such as tissue damage. The cell to cell adhesion process is regulated by specific types of receptors. The mode of action of the composition is to regulate the receptor function with primarily an antagonistic effect. The abovementioned processes often involve cell damage and cell destruction caused by certain enzymes such as hydrolases, proteases and the alike. Many of these enzymes, for example lysosomal enzymes are activated via processes involving receptor interactions. The use of the method according to the invention also results in an interaction with these types of receptors with a beneficial regulation as a consequence.

The invention will be further explained in connection with the following examples. Examples 1-4 show the production of $IP_3$ where as examples 5 and 6 illustrate the preparation of solutions and tablets of $IP_3$. Example 7 relates to the reduction of oedema formation by treatment with $IP_3$. The preventive effect of $IP_3$ against bleeding is described in example 8 whereas example 9 teaches the beneficial use of $IP_3$ against damages caused by burns. Example 10 describes the reduction of vascular leakage when $IP_3$ is used. Examples 11-13 relate to the effect of $IP_3$ on different types of bone disorders.

EXAMPLE 1

Hydrolysis of sodium phytate with baker's yeast and fractionation of a mixture of inositol phosphates.

A 1.4 kg quantity of sodium phytate (from corn, Sigma Chemical Co) was dissolved in 1 200 l sodium acetate buffer pH 4.6. 100 kg of baker's yeast from Jästbolaget, Sweden (dry substance: 28%, nitrogen content: 2%, phosphorus content: 0.4% was added with stirring and incubation was continued at 45° C. The dephosphorylation was followed by determining the inorganic phosphorus released. After 7 hours when 50% inorganic phosphorus was liberated the hydrolysis was stopped by adding ammonia to pH 12. The suspension was centrifuged and the supernatant was collected.

800 l of the supernatant was passed through an ion-exchange column (Dowex 1, chloride form, 100 cm×150 cm) and eluted with a linear gradient of hydrochloric acid (0–0.7 N HCL).

EXAMPLE 2

Structural determination of isomers of inositoltrisphoshate.

The fraction obtained in example 1 with a phosphorus/inositol ratio of three to one was neutralized and precipitated as a calciumsalt. 100 mg of the precipitate was analyzed with H-NMR. Data show that the peak consists of myo-inositol-1.2.6-trisphosphate.

EXAMPLE 3

A 0.5 gram quantity of D-chiro-inositol was dissolved in 1 ml phosphoric acid at 60° C. 20 g polyphosphoric acid was added and the mixture was heated to 150° C. under vacuum for 6 hours. The mixture was diluted with water to a volume of 200 ml and passed through an ion-exchange column (Dowex 1, chloride form, 25 mm×250 mm) and eluted with a linear gradient of hydrochloric acid (0–2.0 N HCl).

The content of the peak with the ratio of phosphorus to inositol of six to one was precipitated by addition of calciumhydroxide. The precipitate was filtered, washed and mixed with 10 ml of a cation-exchange resin to give the acid form of the inositolhexaphosphate. After neutralization with sodium hydroxide and freeze-drying the sodium salt of D-chiro-inositolhexaphosphate was obtained.

EXAMPLE 4

A 0.8 gram quantity of the sodium salt of D-chiro-inositolhexaphosphate produced according to Example 3 was dissolved in 300 ml sodium acetate buffer, pH 5.2. 1.3 gram wheat phytase (EC 3.1.3.26, 0.015 U/mg from Sigma Chemical Co.) was added and the mixture was incubated at 38° C.

After the liberation of 50% inorganic phosphorus the hydrolysis was stopped by adding ammonia to pH 12.

The mixture containing D-chiro-inositolphosphates was passed through an ion-exchange column (Dowex 1 chloride form, 25 mm×250 mm) and eluted with a linear gradient of hydrochloric acid (0–0.7N HCL).

The peak with the ratio of phosphorus to inositol of three to one was neutralized with 1.0M sodium hydroxide and freeze-dried.

Stuctural determination with NMR and IR showed the product to be D-chiro-inositoltrisphosphate.

EXAMPLE 5

Solution of sodium salt of D-myo-inositol-1.2.6-trisphosphate for injection.

0.5 g of the sodium salt of $IP_3$ and 0.77 g NaCl were dissolved in 98.73 ml of water for injection to form a solution suitable for injection into a person or an animal.

EXAMPLE 6

Tablets of calcium salt of D-myo-inositol-1.2.6-trisphosphate.

Tablets of the calcium salt of D-myo-inositol-1.2.6-trisphosphate were produced in the following way. 50 g calcium salt of D-myo-inositol-1.2.6-trisphosphate, 132 g lactose and 6 g acacia were mixed. Purified water was then added to the mixture, whereupon the mixing was continued until a suitable consistency was obtained. The mixture was sieved and dried. Then the mixture was blended with 10 g talcum and 2 g magnesium stearate. The mixture was compressed into tablets each weighing 200 mg.

EXAMPLE 7

Injection of carrageenan into the subplanar surface of the rat hind-paw induces a tissue damage that results in pronounced oedema. The degree of oedema can be reproducibly quantified by measuring paw circumference.

Two groups of five male rats were injected 2 hours and 1 hour before injection of carrageenan with 1000 mg/kg D-myo-inositol-1.2.6-trisphosphate (IP$_3$) or Krebs ringer solution (control) respectively.

Measurement of the paw diameter was made at hourly intervals.

The results show that an injection of IP$_3$ reduces the oedema with 40% four hours after the induction of the damage as compared to control. Thus, the oedema in the IP$_3$-treated animals was strongly reduced.

EXAMPLE 8

Vascular permeability and bleeding induced by histamine in the hamster cheek pouch was determined in the presence of D-myo-inositol-1.2.6-trisphosphate (IP$_3$) compared to control.

Male hamsters were fasted overnight and anaesthetised with sodium pentobarbitone. Infusion was performed through the jugular vein. Injection of histamine (2.7 mg,/kg) was preceded by either saline (control) or IP$_3$ (5.0 mg/kg). The cheek pouch was observed with a microscope for a period of 80 minutes and the number of bleeding sites (petechiae) was recorded before the commencement of the infusion of histamine and at the end of the 80 min period.

The results are shown in the following table:

| Treatment | number of animals | number of petechiae | % inhibition |
|---|---|---|---|
| Saline (control) | 10 | 8.4 | — |
| IP$_3$ | 6 | 1.0 | 88 |

It can be seen that IP$_3$ is an effective compound against vascular permeability and bleeding.

EXAMPLE 9

A controlled burn damage is induced in rats as a heat probe is applied to the skin of the abdomen with a constant pressure. The probe has a surface temperature of 45° C. and is allowed to deliver a specific amount of energy until the temperature is lowered to 37° C. 15 minutes after the induction of the burn an injection of saline (control) or D-myo-inositol-1.2.6-trisphosphate (IP$_3$) was performed. After this first injection (10 mg/kg IP$_3$) an infusion of 0.2 mg/min IP$_3$ followed for 2 hours. 90 minutes after the damage Evans Blue is injected to the animals. This compound binds to albumin, which leaks into the damaged tissue. The amount of albumin leakage is then easily determined by measuring the intensity of colour of Evans Blue in different parts of the tissue. After another 30 minutes the animals are killed and the tissue damage is determined. In the IP$_3$-treated animals (n=10) the burn damage was significantly reduced compared to control (n=10). Thus IP$_3$ is an protective substance against tissue damage caused by burns.

EXAMPLE 10

Local oedema formation is measured in the shaved dorsal skin of rabbits in response to mediators of increased microvascular permeability, such as histamine, bradykinin and platelet activating factor (PAF). When a vasodilator such as calcitonin gene-related peptide (CGRP) is administered together with the mediators the blood flow is increased and this system is established for testing compounds that reduces oedema formation.

Prior to injection of the different mediators Evans Blue is injected into the anaesthetized animals. The distribution of Evans Blue is a measurement of the tissue damage and oedema formation. Directly after injection of the mediators either saline (control) or 50 mg/kg of D-myo-inositol-1.2.6-trisphosphate (IP$_3$) are performed.

The results are shown below as per cent inhibition of IP$_3$ compared to control.

| Mediator | % inhibition with IP$_3$ compared to control |
|---|---|
| Bradykinin | 64 |
| Histamine | 61 |
| PAF | 64 |

As can be seen the presence of IP$_3$ significantly reduces the oedema formation.

EXAMPLE 11

Injection of Freund's complete adjuvant into rats results in the development of different forms of bone disorders. 13 male rats weighing approximately 200 grams were divided into two groups. The animals in both groups were anaesthetized with halothane and injected intradermally at the tail base with 0.1 ml adjuvant solution (Myo-bacterium butylricum, 10 mg/ml in paraffin oil) at day 0. The seven rats in Group 1 received daily subcutaneous injections of 50 mg D-myo-inositol-1.2.6-trisphosphate (IP$_3$) during the experiment (25 days) while the six rats in Group 2 served as a control and received daily injections with saline. At the end of the experiment the animals were killed and the left hind limbs were fixed in a saline-solution, washed in water, dried and x-rayed. The x-ray unit is of the microfocal type and the produced radiographs have a magnification of ×10. Each radiograph was graded blindly for the presence and severity of bone mineralization with the following grades:

| Grade 0: | Normal |
|---|---|
| Grade 1: | Mild articular osteoporosis |
| Grade 2: | Severe generalized osteoporosis with pathological fractures |

The results are shown in the following table:

| Animals no. | 1 | 2 | 3 | 4 | 5 | 6 | 7 | |
|---|---|---|---|---|---|---|---|---|
| Group 1 | 0 | 1 | 1 | 1 | 0 | 1 | 1 | (grade) |
| Group 2 | 1 | 2 | 1 | 1 | 0 | 2 | — | (grade) |

As can be seen the IP$_3$-treatment (Group 1) reduces the occurence and severity of osteoporosis compared to control (Group 2).

EXAMPLE 12

The x-rays obtained as described in example 7 were graded blindly for the presence and severity of bone erosions with the following grades:

| Grade 0: | Normal |
|---|---|
| Grade 1. | Small bony irregulations at corners of articular surfaces |
| Grade 2: | Complete destruction of the articular surfaces |

The results are shown in the following table:

| Animal no. | 1 | 2 | 3 | 4 | 5 | 6 | 7 | |
|---|---|---|---|---|---|---|---|---|
| Group 1 | 0 | 1 | 1 | 0 | 1 | 0 | 0 | (grade) |
| Group 2 | 1 | 2 | 2 | 1 | 1 | 2 | — | (grade) |

The $IP_3$-treatment (Group 1) reduces the occurence and severity of bone erosion compared to control (Group 2).

EXAMPLE 13

The x-rays obtained as described in example 7 were graded blindly for the presence and severity of periostitis with the following grades:

| Grade 0: | Normal |
|---|---|
| Grade 1: | Thin layers of new bone |
| Grade 2: | Severe irregular bony proliferation |

The results are shown in the following table:

| Animal no. | 1 | 2 | 3 | 4 | 5 | 6 | 7 | |
|---|---|---|---|---|---|---|---|---|
| Group 1 | 1 | 1 | 1 | 1 | 0 | 0 | 0 | (grade) |
| Group 2 | 0 | 2 | 2 | 1 | 1 | 1 | — | (grade) |

The $IP_3$-treatment (Group 1) reduces the occurence and severity of periostitis compared to control (Group 2).

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A method in preventing or alleviating bone damage comprising administering, to a mammal in need thereof, a bone damage preventing or alleviating effective amount of a pharmaceutical composition which includes at least one isomer of inositol triphosphate.

2. A method in accordance with claim 1 wherein said pharmaceutical composition includes at least one salt of an isomer of inositol triphosphate.

3. A method in accordance with claim 2 wherein said salt of said isomer of inositol trisphosphate is a sodium, a potassium, a calcium or a zinc salt.

4. A method in accordance with claim 1 wherein said pharmaceutical composition is provided in tablet form.

5. A method in accordance with claim 1 wherein said pharmaceutical composition is provided in granular form.

6. A method in accordance with claim 1 wherein said pharmaceutical composition is provided in solution form.

7. A method in accordance with claim 1 wherein said isomer is selected from the group consisting of D-myo-inositol-1,2,6-trisphosphate, myo-inositol-1,2,3-trisphosphate and L-myo-inositol-1,3,4-trisphosphate.

8. A method in accordance with claim 7 wherein said D-myo-inositol-1,2,6-trisphosphate is provided as the sodium, the potassium, the calcium or the zinc salt.

* * * * *